(12) United States Patent
Zhao et al.

(10) Patent No.: US 11,467,080 B2
(45) Date of Patent: Oct. 11, 2022

(54) ESTIMATING PERMEABILITY OF RESERVOIR ROCKS USING MERCURY INJECTION CAPILLARY PRESSURE

(71) Applicant: Saudi Arabian Oil Company, Dhahran (SA)

(72) Inventors: Hongwen Zhao, Beijing (CN); Yufeng Cui, Beijing (CN); Ming Zhang, Beijing (CN); Peng Lu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 129 days.

(21) Appl. No.: 16/989,551

(22) Filed: Aug. 10, 2020

(65) Prior Publication Data

US 2022/0042898 A1 Feb. 10, 2022

(51) Int. Cl.
*G01N 15/08* (2006.01)
*G01N 33/24* (2006.01)

(52) U.S. Cl.
CPC ......... *G01N 15/0826* (2013.01); *G01N 33/24* (2013.01)

(58) Field of Classification Search
CPC .... G01N 15/00; G01N 15/08; G01N 15/0826; G01N 33/24
See application file for complete search history.

(56) References Cited

U.S. PATENT DOCUMENTS

| 2,724,963 | A | * | 11/1955 | Ten Brink | G01N 15/0826 73/38 |
| 4,211,106 | A | * | 7/1980 | Swanson | G01N 15/0886 73/38 |
| 4,542,648 | A | | 9/1985 | Vinegar et al. | |
| 4,628,468 | A | | 12/1986 | Thompson et al. | |
| 4,648,261 | A | | 3/1987 | Thompson et al. | |

(Continued)

FOREIGN PATENT DOCUMENTS

CN 106442262 A * 2/2017 ............. G01N 15/08

OTHER PUBLICATIONS

"Application of mercury injection capillary pressure to mudrocks" Peng et al; Marine and Petroleum Geology 88 (2017) 30-40; Aug. 2017.*

(Continued)

*Primary Examiner* — Nguyen Q. Ha
(74) *Attorney, Agent, or Firm* — Fish & Richardson P.C.

(57) ABSTRACT

Methods of estimating permeability of reservoir rocks using mercury injection capillary pressure can include: receiving mercury injection capillary pressure test data and porosity data for a core sample; determining a fractal dimension (D) for the core sample based on the received mercury injection capillary pressure test data for the core sample; determining a pore throat radius ($R_d$) for the core sample; determining a composite parameter ($\beta$) for the core sample where $$\beta = \frac{\phi R_d}{(D-2)};$$

and estimating permeability (K) of the core sample based on a relationship of $\ln(K)$ as a function of $\ln(\beta)$ determined by performing a regression analysis data from other core samples from the reservoir.

20 Claims, 7 Drawing Sheets

FIG. 6

(56) References Cited

U.S. PATENT DOCUMENTS

| | | | |
|---|---|---|---|
| 4,893,504 A * | 1/1990 | O'Meara, Jr. .......... | G01N 15/08 |
| | | | 378/68 |
| 5,069,065 A | 12/1991 | Sprunt et al. | |
| 6,088,656 A | 7/2000 | Ramakrishnan et al. | |
| 6,229,308 B1 | 5/2001 | Freedman | |
| 6,977,499 B2 | 12/2005 | Kiesl et al. | |
| 6,987,385 B2 | 1/2006 | Akkurt et al. | |
| 7,363,158 B2 | 4/2008 | Stelting et al. | |
| 7,970,545 B2 | 6/2011 | Sanstrom | |
| 8,385,604 B2 | 2/2013 | Orpen | |
| 8,605,951 B2 | 12/2013 | Baggs et al. | |
| 9,081,117 B2 | 7/2015 | Wu et al. | |
| 2007/0239359 A1 | 10/2007 | Stelting et al. | |
| 2010/0198638 A1 | 8/2010 | Deffenbaugh et al. | |
| 2010/0305927 A1 | 12/2010 | Suarez-Rivera et al. | |
| 2012/0221306 A1 | 8/2012 | Hurley et al. | |
| 2013/0080133 A1 | 3/2013 | Sung et al. | |
| 2013/0259190 A1 | 10/2013 | Walls et al. | |
| 2013/0297272 A1 | 11/2013 | Sung et al. | |
| 2015/0198036 A1 | 7/2015 | Kleinberg et al. | |
| 2018/0320514 A1 | 11/2018 | Felkl et al. | |
| 2021/0116354 A1* | 4/2021 | Khodja .............. | G01N 15/0886 |

OTHER PUBLICATIONS

Ding et al., "Fractal dimension of pore space in carbonate samples from Tushka area (Egypt)" Arabian Journal of Geosciences 10.17, Sep. 2017, 12 pages.

Li et al., "New fractal-dimension-based relation model for estimating absolute permeability through capillary pressure curves." Journal of Petroleum Science and Engineering 196, Jan. 2021, 16 pages.

Zhang et al., "Fractal dimension of pore-space geometry of an Eocene sandstone formation." Geophysics 79.6, Nov. 2014, D377-D387, 11 pages.

PCT International Search Report and Written Opinion in International Appln. No. PCT/US2021/045376, dated Nov. 26, 2021, 15 pages.

Brown, "Posity Variation in Carbonates as a Function of Depth: Mississippian Madison Group, Williston Basin," Chapter 3, found in Kupecz et al., Reservoir quality prediction in sandstones and carbonates, AAPG Memoir 69, Jan. 1, 1997, 8 pages.

Buiting et al., "Permeability from porosimetry measurements: Derivation for a tortuous and fractal tubular bundle." Journal of Petroleum Science and Engineering 108, 2013, 267-278, 12 pages.

Carey et al., "Analysis of water hammer signatures for fracture diagnostics." SPE-174866-MS, SPE Annual Technical Conference and Exhibition, Society of Petroleum Engineers, 2015, 25 pages.

Clerke et al., "Application of Thomeer Hyperbolas to decode the pore systems, facies and reservoir properties of the Upper Jurassic Arab D Limestone, Ghawar field, Saudi Arabia: A "Rosetta Stone" approach," GeoArabia 13.4, 2008, 113-160, 48 pages.

DMT, "DMT CoreScan 3 High-Tech Core Logging Tool"; http://www.corescan.de/fileadmin/downloads/DMT_CoreScan3_Info.pdf; Jan. 31, 2013, 1-20, 20 pages.

Dunham et al., "Hydraulic fracture conductivity inferred from tube wave reflections." SEG Technical Program Expanded Abstracts 2017. Society of Exploration Geophysicists, 2017, 947-952, 6 pages.

Enos and Sawatsky, "Pore networks in holocene carbonate sediments," Journal of Sedimentary Research vol. 51, Issue 3, Jan. 1981, 26 pages.

Gaillot et al., "Contribution of Borehole Digital Imagery in Core-Logic-Seismic Integration", Scientific Drilling, No. 5, Sep. 2007,50-53, 4 pages.

Huet et al., "A modified purcell/burdine model for estimating absolute permeability from mercury-injection capillary pressure data." International petroleum technology conference. vol. 10994. International Petroleum Technology Conference, 2005, 39 pages.

Jia et al., "Comparison of Three Capillary Fractal Models for Reservoir Evaluation." Electronic Journal of Geotechnical Engineering 21.5, Jan. 2016, 1977-1986, 9 pages.

Kewen, "Characterization of rock heterogeneity using fractal geometry." ,SPE 86975, SPE International Thermal Operations and Heavy Oil Symposium and Western Regional Meeting. Society of Petroleum Engineers, 2004, 7 pages.

Lander and Walderhaug, "Predicting Porosity through Simulating Sandstone Compaction and Quartz Cementation," AAPG Bulletin, vol. 83, No. 3, Mar. 1999, 17 pages.

Liang et al., "Hydraulic fracture diagnostics from Krauklis-wave resonance and tube-wave reflections." Geophysics 82.3, 2017, D171-D186, 16 pages.

Liu et al., "Determining the segmentation point for calculating the fractal dimension from mercury injection capillary pressure curves in tight sandstone." Journal of Geophysics and Engineering 15.4, Aug. 2018, 1350-1362, 13 pages.

Office Action issued in GCC Application No. 2015/29123 dated Jan. 10, 2018, 5 pages.

Paulsen et al., "A Simple Method for Orienting Drill Core by Correlating Features in Whole-Core Scans and Oriented Borehole-Wall Imagery" Journal of Structural Geology; Published in 2002, 1233-1238, 6 pages.

PCT International Search Report and Written Opinion of the International Searching Authority issued in International Application No. PCT/US2015/022492 dated Aug. 4, 2015, 11 pages.

Pittman et al., "Relationship of Porosity and Permeability to Various Parameters Derived from Mercury Injection-Capillary Pressure Curve for Sandstone" AAPG Bulletin 76.2, Feb. 1992, 8 pages.

Purcell, "Capillary pressures-their measurement using mercury and the calculation of permeability therefrom," Journal of Petroleum Technology, 1.02, Feburary 1949, 39-48, 10 pages.

Schmoker, "Empirical Relation Between Carbonate Porosity and Thermal Maturity: An Approach to Regional Porosity Prediction," The American Association of Petroleum Geologists, vol. 68, No. 11, Nov. 1984, 7 pages.

Swanson, "A Simple Correlation Between Permeabilities and Capillary Pressures" Journal of Petroleum Technology, Dec. 1981, 2498-2504, 7 pages.

Tang et al., "A dynamic model for fluid flow in open borehole fractures" Journal of Geophysical Research: Solid Earth, 94(B6), 7567-7576, 10 pages.

Teagle et al., "Methods" Proceedings of the Integrated Ocean Drilling Program, vol. 309/312; Published in 2006, 1-70, 70 pages.

Thomeer, "Introduction of a Pore Geometrical Factor Defined by the Capillary Pressure Curve", Petroleum Transactions of the AIME, Mar. 1960, 73-77, 5 pages.

Wang et al., "Analysis of Pore Size Distribution and Fractal Dimension in Tight Sandstone with Mercury Intrnsion Porosimetry" Results in Physics 13, Jun. 2019, 10 pages.

WellCAD Software, "4.4 Book 1—Basics," V2011.10.17, ALT, Oct. 17, 2011, 11 pages.

Wilkens et al., "Data Report: Digital Core Images as Data: An Example from IODP Expedition 303", Proceedings of the Integrated Ocean Drilling Program, vol. 303/306; Published in 2009, 1-16, 16 pages.

Zhang et al., "Modeling carbonate diagenesis for reservoir quality prediction: Predicting cementation and compaction from mud content using petrographic data from carbonate reservoir in a giant oil field," AAPG, Aug. 3, 2016, 1 page.

* cited by examiner

ESTIMATING PERMEABILITY OF RESERVOIR ROCKS USING MERCURY INJECTION CAPILLARY PRESSURE

TECHNICAL FIELD

The present disclosure generally relates to estimating permeability of reservoir rocks, particularly estimating permeability of reservoir rocks based using mercury injection capillary pressure data.

BACKGROUND

Permeability is the ability, or measurement of a rock's ability, to transmit fluids, typically measured in darcies or millidarcies. Formations that transmit fluids readily, such as sandstones, are described as permeable and tend to have many large, well-connected pores. Impermeable formations, such as shales and siltstones, tend to be finer grained or of a mixed grain size, with smaller, fewer, or less interconnected pores. Absolute permeability is the measurement of the permeability conducted when a single fluid, or phase, is present in the rock. Effective permeability is the ability to preferentially flow or transmit a particular fluid through a rock when other immiscible fluids are present in the reservoir (for example, effective permeability of gas in a gas-water reservoir). The relative saturations of the fluids as well as the nature of the reservoir affect the effective permeability. Relative permeability is the ratio of effective permeability of a particular fluid at a particular saturation to absolute permeability of that fluid at total saturation. Calculation of relative permeability allows for comparison of the different abilities of fluids to flow in the presence of each other, since the presence of more than one fluid generally inhibits flow. Understanding the permeability of a formation is important to assessing whether hydrocarbons present in the formation can be produced on a cost-effective basis and managing field operations after production begins.

Mercury injection capillary pressure (MICP) is a technique for measurements of porosity, pore throat size distribution, and injection pressure vs. mercury saturation for many types of rocks. The latter two are correlated to and can be used to estimate permeability.

SUMMARY

This specification describes an approach to modeling the permeability of carbonate reservoir rocks. This approach extracts pore structure and pore fractal dimension information from MICP results. The MICP tests can be performed using a porosimeter (for example, a M9145 Porosimeter commercially available from Grace Instruments of Houston, Tex.). In some cases, this approach uses previously generated MICP data found in special core analysis datasets to extract pore structure and pore fractal dimension information.

In one aspect, methods of estimating permeability of reservoir rocks using mercury injection capillary pressure include: taking a plurality of core samples from a reservoir; performing mercury injection capillary pressure tests to develop a capillary pressure curve for each of the plurality of core samples; determining a pore throat radius ($R_d$) for each of the plurality of core samples; determining a fractal dimension (D) of each of the plurality of core samples; measuring porosity ($\emptyset$) of each of the plurality of core samples; determining a composite parameter ($\beta$) for each of the plurality of core samples, where $$\beta = \frac{\emptyset R_d}{(D-2)};$$

measuring the permeability (K) of each of the plurality of core samples; performing a regression analysis to determine a relationship of ln(K) as a function of ln($\beta$); and determining the composite parameter ($\beta$) for other locations in the reservoir and estimating permeability (K) at the other locations in the reservoir based on the determined relationship.

In one aspect, methods of estimating permeability of reservoir rocks using mercury injection capillary pressure include: receiving mercury injection capillary pressure test data and porosity data for a core sample; determining a fractal dimension (D) for the core sample based on the received mercury injection capillary pressure test data for the core sample; determining a pore throat radius ($R_d$) for the core sample; determining a composite parameter ($\beta$) for the core sample where $$\beta = \frac{\emptyset R_d}{(D-2)};$$

and estimating permeability (K) of the core sample based on a relationship of ln(K) as a function of ln($\beta$) determined by performing a regression analysis data from other core samples from the reservoir.

Embodiments of these methods can include one or more of the following features.

In some embodiments, the core sample is one of a plurality of core samples and receiving mercury injection capillary pressure test data and porosity data comprises receiving mercury injection capillary pressure test data and porosity data for each of the plurality of core samples.

In some embodiments, the plurality of core samples includes at least one core sample from multiple depositional textures present in the reservoir.

In some embodiments, the plurality of core samples includes at least one grainstone core sample, at least one packstone core sample, at least one wackestone core sample, and at least one bindstone core sample.

In some embodiments, methods also include determining the pore throat radius ($R_d$) for each of the plurality of core samples.

In some embodiments, determining the pore throat radius ($R_d$) for each of the plurality of core samples comprises determining an entry pressure of the largest pore subsystem from the mercury injection capillary pressure tests and calculating the associated the pore throat radius ($R_d$) using Washburn's equation.

In some embodiments, methods also include determining a fractal dimension (D) of each of the plurality of core samples.

In some embodiments, determining a fractal dimension (D) of each of the plurality of core samples comprises determining a slope of a curve of ln $S_{Hg}$ as a function of ln $P_c$ where $S_{Hg}$ is mercury saturation and $P_c$ is capillary pressure.

In some embodiments, methods also include measuring porosity ($\emptyset$) of each of the plurality of core samples.

In some embodiments, methods also include determining a composite parameter ($\beta$) for each of the plurality of core samples, where $$\beta = \frac{\emptyset R_d}{(D-2)};$$

In some embodiments, methods also include measuring the permeability (K) of each of the plurality of core samples.

In some embodiments, methods also include performing a regression analysis to determine a relationship of ln(K) as a function of ln(β).

These systems and methods provide a quick way to use MICP data to model permeability of carbonate rocks. The underlying MICP data can be generated using commercially available equipment. For many fields, MICP data is available on special core analysis datasets that are commonly used by oil companies. The parameters used in this approach can be easily extracted from MICP data without requiring fitting parameters. This approach has demonstrated the ability to model permeability and formation factor of heterogeneous carbonate rocks that are formed within various depositional and diagenetic environments. This approach is particularly useful for carbonate rocks because carbonate rocks have complicated pore structures (e.g., moldic porosity, microporosity, vugs and fractures). As a result, no simple correlation can be found for permeability as a function of porosity and the traditional permeability modeling does not work for carbonate rocks. This MICP-based approach provides an effective permeability modeling method for carbonate rocks.

Predicting petrophysical properties of heterogeneous carbonate reservoir rocks is important for many geological and engineering problems including reserve estimation, geological modeling, reservoir simulation, production, water flooding, and enhanced oil recovery. This approach provides a quick and easy way to model permeability of carbonate reservoir rocks, which can be used for complex reservoir-related technical challenges including reserve estimation in complex carbonate reservoirs pay zones with low resistivity and low contrast well log responses.

This approach can predict permeability of carbonate rocks based on MICP data with a high accuracy because it integrates both pore complexity (fractal dimension), pore size distribution (entry pore throat size) and pore volume (porosity). By combining fractal dimension, entry pore throat of largest pore subsystem and porosity extracted from MICP data, this approach can predict both permeability and formation factor. Formation factor (F) is the ratio of resistivity of a rock filled with water (Ro) to the resistivity of that water (Rw) (i.e., F=Ro/Rw). This method is suitable for predicting permeability of heterogeneous carbonate reservoir rocks that have various depositional and diagenetic textures. This method is easier to apply than methods often need many fitting parameters and time-consuming calibrations.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

This specification describes an approach to modeling the permeability of carbonate reservoir rocks. This approach extracts pore structure and pore fractal dimension information from MICP results. The MICP tests can be performed using a porosimeter (for example, a M9145 Porosimeter commercially available from Grace Instruments of Houston, Tex.). In some cases, this approach uses previously generated MICP data found in special core analysis datasets to extract pore structure and pore fractal dimension information.

These systems and methods provide a quick way to use MICP data to model permeability of carbonate rocks. The underlying MICP data can be generated using commercially available equipment. For many fields, MICP data is available on special core analysis datasets that are commonly used by oil companies. The parameters used in this approach can be easily extracted from MICP data without requiring fitting parameters. This approach has demonstrated the ability to model permeability and formation factor of heterogeneous carbonate rocks that are formed within various depositional and diagenetic environments.

Figure 1:
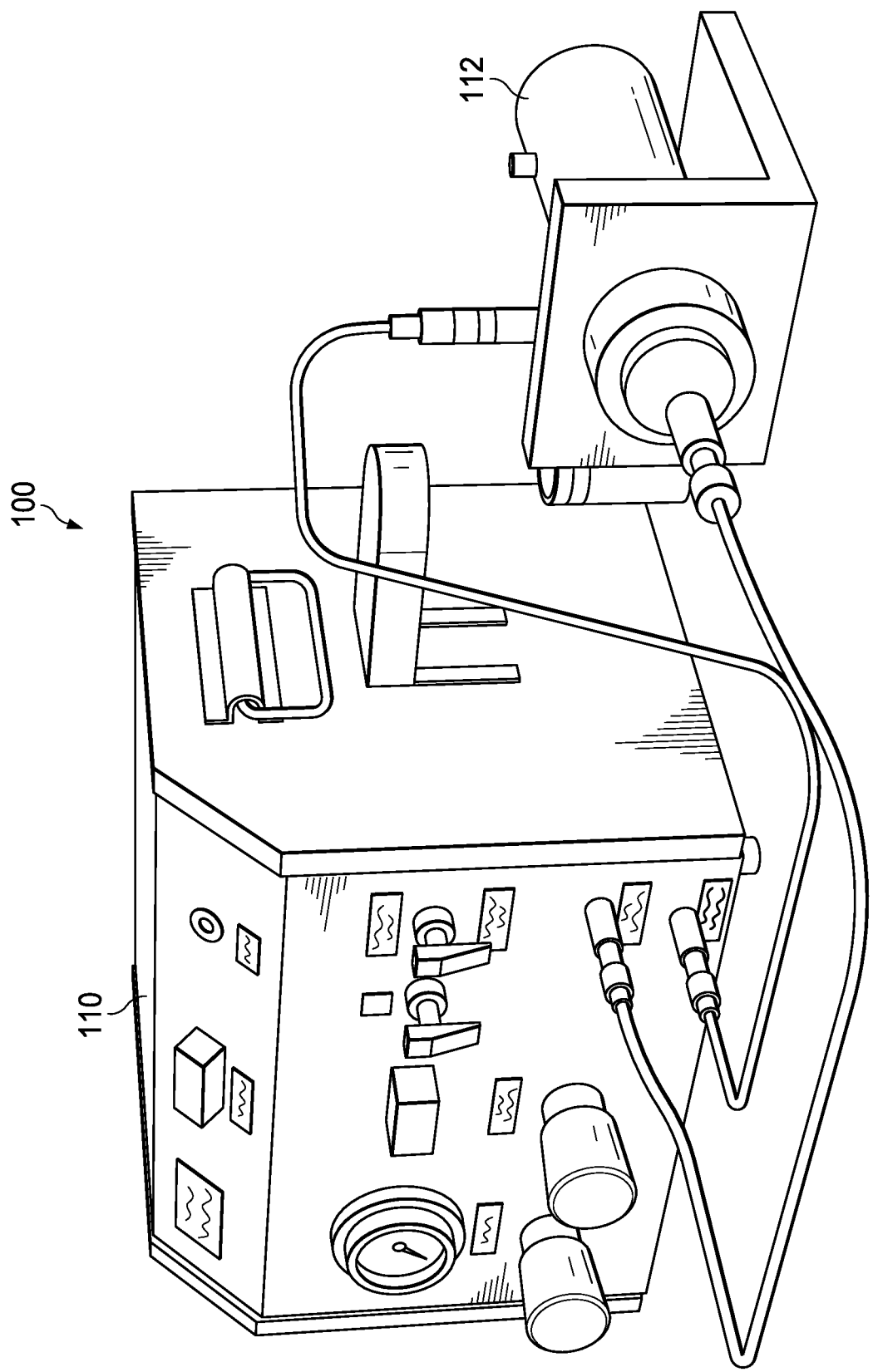
FIG. 1 is a schematic view of a porosimeter for performing MICP tests.

FIG. 1 is a schematic view of a porosimeter 100 for performing MICP tests. The porosimeter 100 includes a main unit 110 and core chamber 112 sized to receive a core sample (e.g., a core sample taken from a subsurface formation of a potential hydrocarbon reservoir). Mercury can be used for capillary pressure tests because mercury is normally a non-wetting fluid and will not readily enter small pores in the core without the application of external pressure.

To perform a MICP test, a cleaned, dried core sample is inserted into the core chamber 112. Air is evacuated from the core chamber 112 to provide a vacuum. The pressure in the system, effectively the differential across the mercury/vacuum interface, is raised in stages to force mercury enter progressively smaller pores of the core sample. The volume of mercury, which has entered the pores at each pressure, is determined from volumetric readings, and the proportion of the pore space filled is calculated. This procedure is continued until the core sample is filled with mercury or the injection pressure reach to some pre-determined value. It is possible to calculate the average size of the pores making up a stated fraction of the total pore space from the capillary pressure curve. The volume of mercury injected into the pores at a given pressure is usually expressed as a proportion of the total pore space, and is presented as a pore size distribution.

Figure 2:
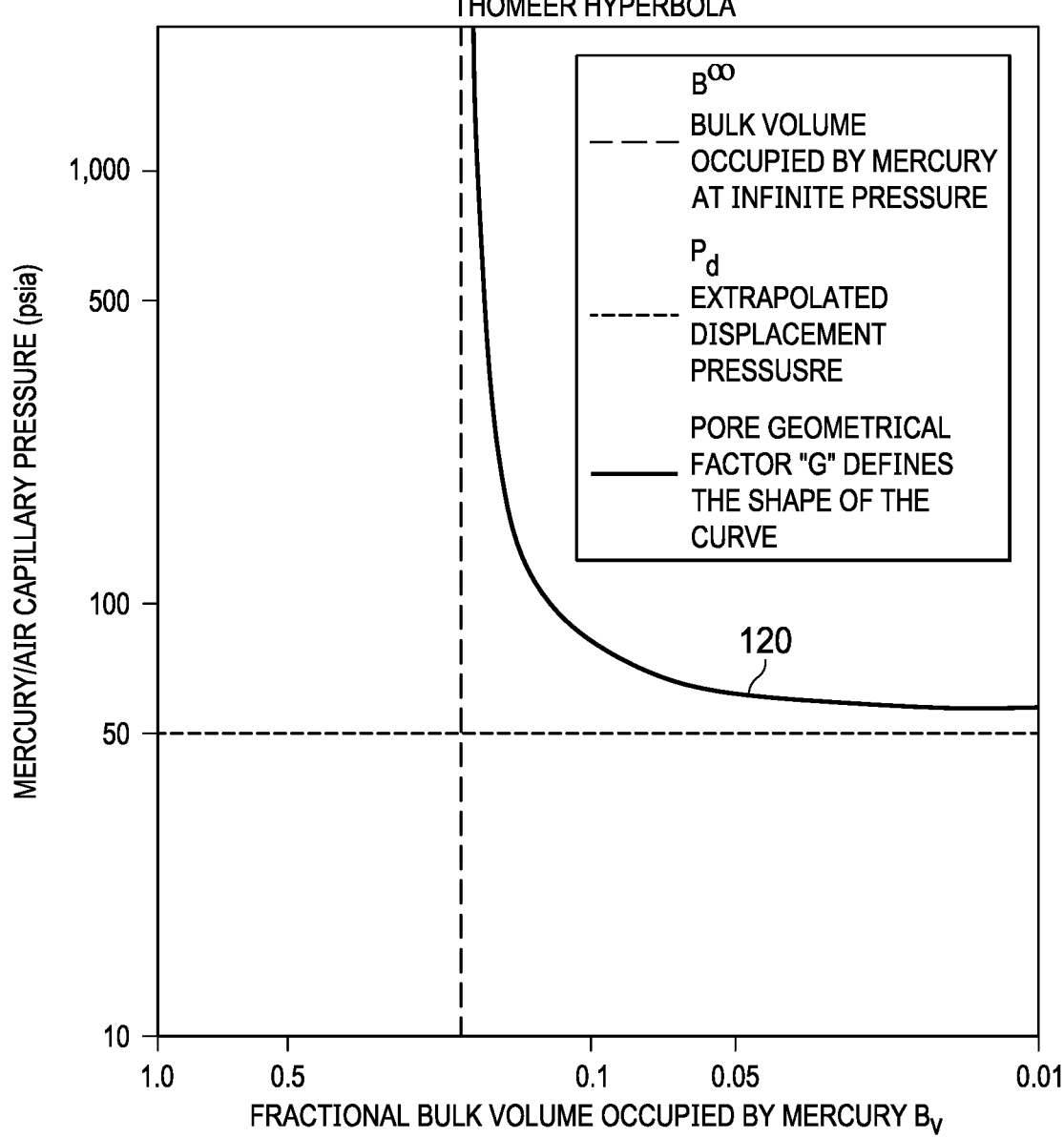
FIG. 2 is a chart illustrating typical MICP curves of carbonate reservoir rocks.

FIG. 2 is a chart illustrating typical MICP curves 120 of carbonate reservoir rocks. The MICP data can be used to calculate the capillary radius within the pore network of the rocks. The capillary radius (pore throat radius) can be calculated with Washburn's equation (Washburn, 1921):

$$P_c = \frac{2\sigma\cos\theta}{r} \quad (1)$$

where $P_c$ is the capillary pressure, a is the interfacial tension, $\theta$ is the contact angle, expressing wettability, r is the capillary radius. The MICP curves 120 used to test the approach described in this specification were measured on core plugs with a mercury intrusion porosimeter that had the maximum intrusion pressure of 60,000 pounds per square inch (psi). The capillary pressure versus mercury saturation can be plotted on a semi-log plot as shown in FIG. 2.

Figure 3:
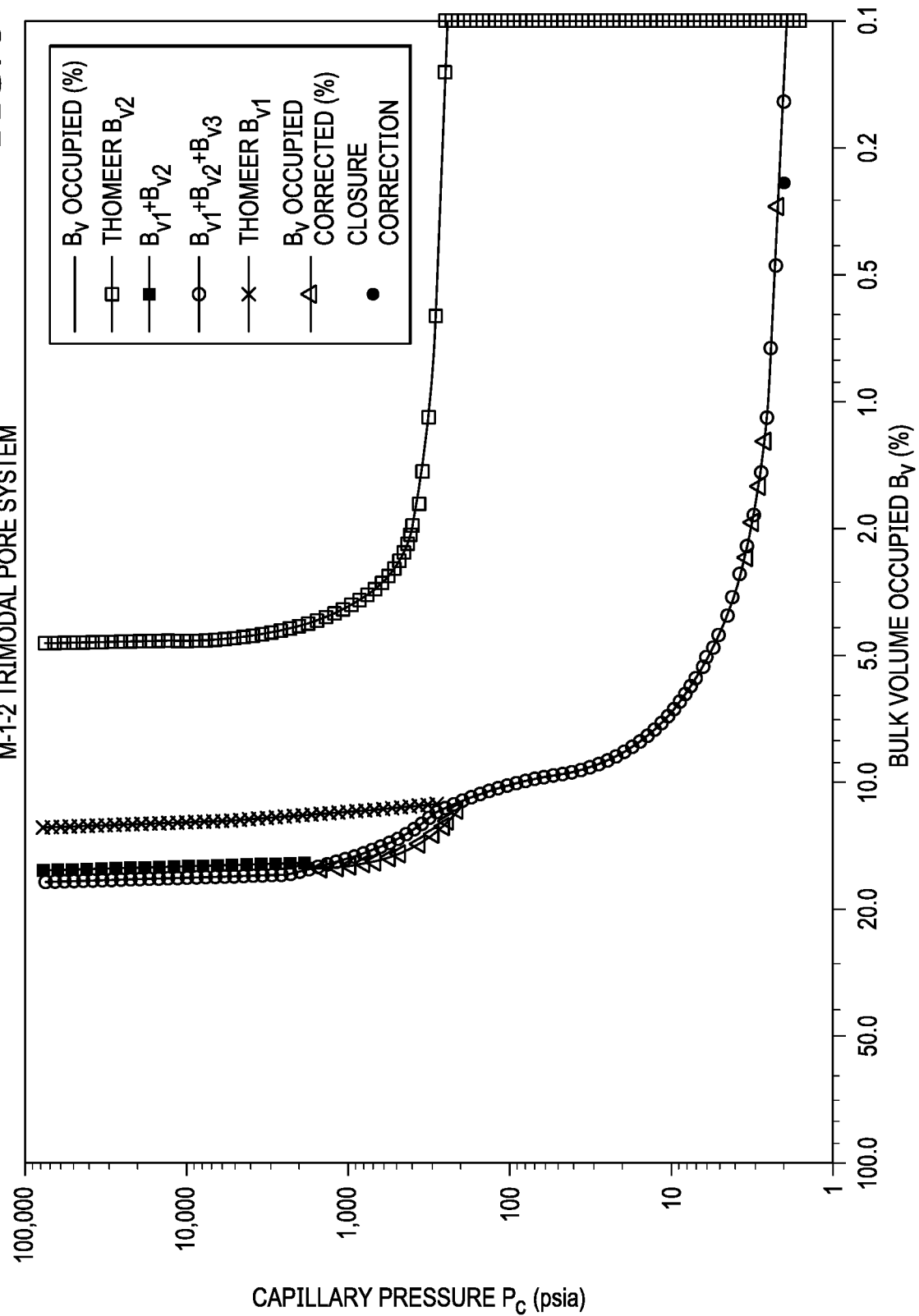
FIG. 3 is a chart illustrating Thomeer hyperbola analysis.

FIG. 3 is a chart illustrating Thomeer hyperbola analysis. The two Y axes are Capillary pressure (Pc) and the height above free water level, respectively. Both of them express the pressure and can be converted to each other.

This analysis can be used to determine the entry pressure of a core sample. Thomeer (1960) proposed that a capillary pressure curve can be describe with a hyperbola curve that is defined as:

$$\log(e^{-G}) = \log\left(\frac{B_v}{B_\infty}\right) \times \log\left(\frac{P_c}{P_d}\right) \quad (2)$$

where G is the shape factor; $B_v$ is the cumulative bulk volume percentage, $B_\infty$ is the matrix mercury bulk volume percentage (i.e., the percent bulk volume occupied by mercury at infinite applied pressure); $P_c$ is the capillary pressure; and $P_d$ is the entry pressure (i.e., the displacement pressure required to first intrude mercury into the largest pore-throat). Clerke et al. (2008) found that the capillary pressure curves of many limestone reservoir rocks have to be described by more than one Thomeer hyperbolas 140. They argued that this phenomenon reflects multi-pore subsystems that these carbonate rocks contain. For each pore subsystem, unique G, $P_d$, and $B_\infty$ can be calculated with a curve fitting technique. In the current methodology, Clerke's technique is used to extract the $P_d$ values of the largest pore system (BV1) of carbonate reservoir rocks as demonstrated by an example on FIG. 2. In practice, $B_v$ and $P_c$ data from the MICP experiment are fit by equation (2) to determine $P_d$, $B_\infty$ and G, for individual samples. The corresponding pore throat radius ($R_d$) is then calculated by using Equation (1). The pore throat radius is ($R_d$) is the capillary radius (r) for a given capillary pressure. An alternative approach is to physically measure Rd with Scanning Electron Microscopy (SEM) or Transmission Electron Microscopy (SEM), but this technology is time consuming and not cost-effective.

The pore spaces of reservoir rocks are fractal in nature. The fractal dimension is believed to reflect the heterogeneity of pore spaces of reservoir rocks.

A fractal object is characterized by its nature of self-affinity with a dimension that is non-integer. This character can be represented mathematically by a power law (Mandelbrol, 1982):

$$N(r) \propto r^{-D} \quad (3)$$

where r is the radius of a unit that fills into a fractal object, N(r) is the number of the units with a radius of r, and D is the fractal dimension.

The fractal dimension of the pore space of formation rocks can be derived from MICP data. For fractal pore spaces, if a capillary tube model is applied, then N(r) can be expressed as:

$$N(r) = \frac{V_{Hg}}{\pi r^2 l} \propto r^{-D} \quad (4)$$

where $V_{Hg}$ is the cumulative volume of intruded mercury; r is capillary radius; and l is the length of a capillary tube. This implies that $$V_{Hg} \propto r^{2-D} \quad (5)$$

By definition, mercury saturation $S_{Hg}$ is the cumulative volume of intruded mercury divided by the pore volume $V_p$ of the core sample $$\left(\text{i.e., } S_{Hg} = \frac{V_{Hg}}{V_p}\right).$$

Combining this definition with Washburn's equation (Equation 1), an equation reflecting the relationship between $S_{Hg}$, capillary pressure $P_c$, and D can be derived as:

$$S_{Hg} = \alpha P_c^{-(2-D)} \quad (6)$$

where $\alpha$ is a constant. Taking the natural log of Equation 6 provides $$\ln S_{Hg} = -(2-D)\ln P_c + \ln \alpha \quad (7)$$

Equation 7 indicates that the fractal dimension D can be calculated based on the slope (m) of a curve of $\ln S_{Hg}$ as a function of $\ln P_c$ near full saturation. More specifically, the slope (m)=$-(2-D)$. The slope (m) can be calculated numerically or by plotting $S_{Hg}$ and $P_c$ on log-log sheet.

Figure 4:
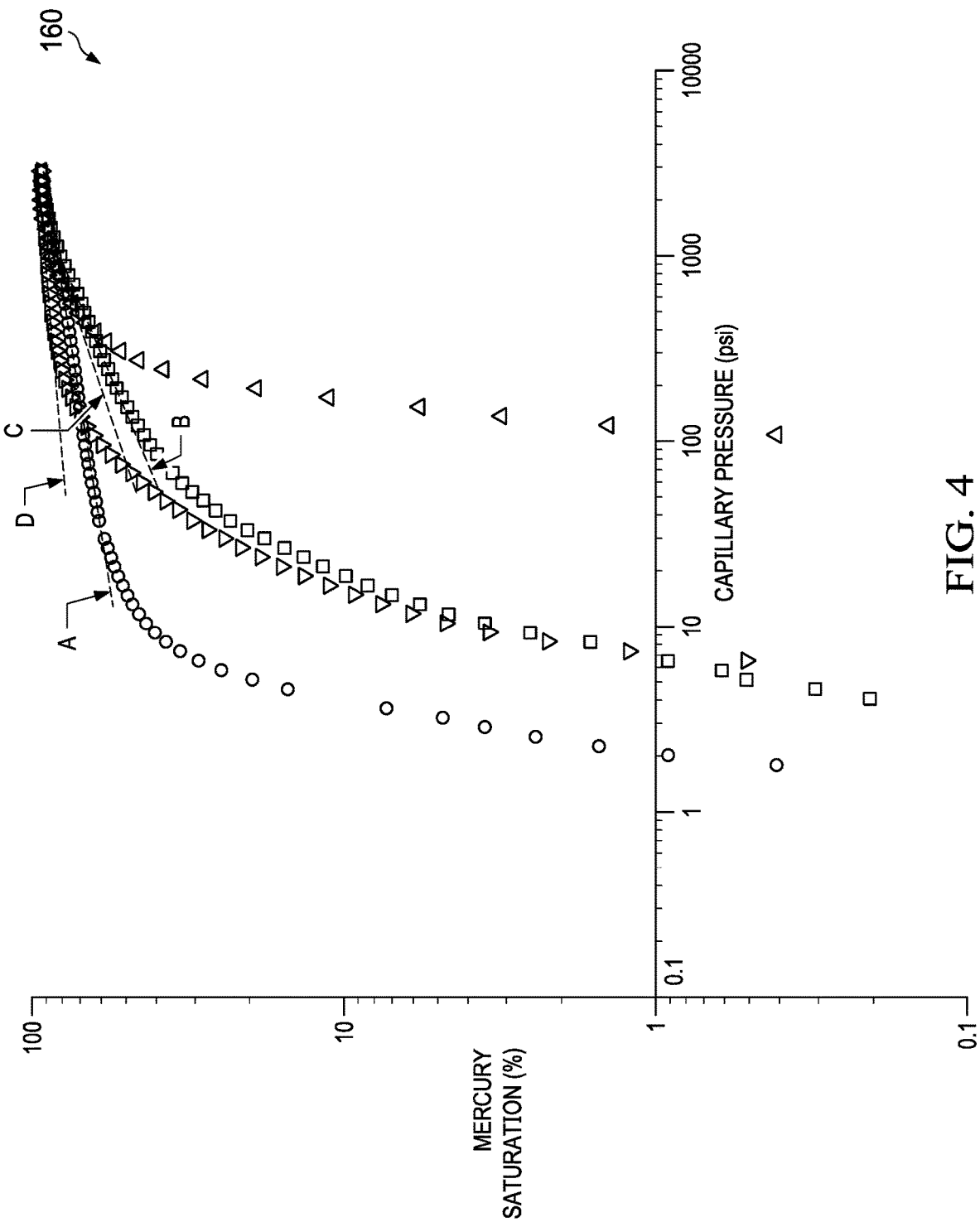
FIG. 4 is chart presenting the fractal dimensions of pore space of carbonate rock samples calculated from MICP data.

FIG. 4 is a chart presenting MICP data 160 showing ln $S_{Hg}$ as a function of ln $P_c$ for 4 core samples (A, B, C, D). For each curve, the slope varies with saturation but, as previously noted, Equation 7 is applicable near full saturation. Accordingly, the slope (m) of a portion of a curve above a cutoff value for $S_{Hg}$ is calculated or measured. In FIG. 4, the apparent linear part of the points is used for slope calculation. The cutoff values are different for different samples. For example, 80% is used for D; 60% is used for A and C; 50% is used for B.

After calculating entry pressure $P_d$ and fractal dimension D, a composite parameter ($\beta$) combining fractal dimension (D), the pore throat radius ($R_d$) corresponding to the entry pressure ($P_d$) of the largest pore subsystem, and the helium porosity ($\emptyset$) can be defined as $$\beta = \frac{\emptyset R_d}{(D-2)} \quad (8)$$

This is an empirical equation without a clear theoretical basis. However, it is known that parameters like D, Rd and porosity impact permeability, so this composite parameter can be used eliminate the scatterness of the permeability model.

Figure 5:
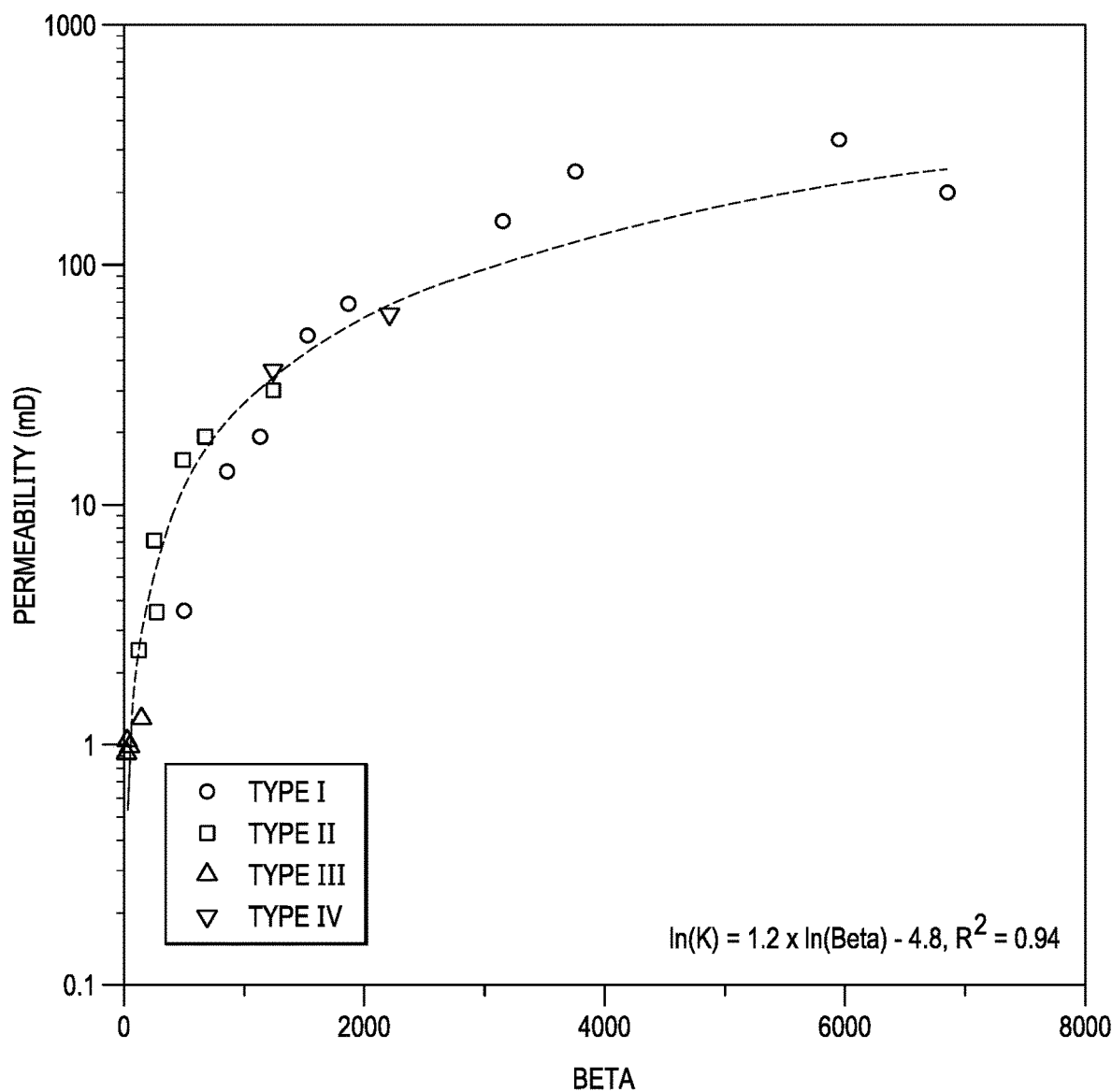
FIG. 5 is a chart illustrating the correlation between permeability and p values of carbonate reservoir rocks.

FIG. 5 is a chart illustrating the correlation between permeability and p values of carbonate reservoir rocks. The composite parameter $\beta$ was generated from a dataset of 21 carbonate samples for which permeability (K) had previously been measured. The 21 carbonate samples included four rock types with different depositional textures. A regression between permeability (K) and the composite parameter $\beta$ provided the relationship $$\ln(K) = 1.2 \times \ln(\beta) - 4.8 \quad (9)$$

A very good correlation exists between permeability and the composite parameter β(R²=0.94) (FIG. 4). Note that the depositional textures of carbonate samples vary from grainstone to mudstone to bindstone. This empirical model provides a new way to accurately estimate the permeability of carbonate reservoir rocks with various depositional textures.

Figure 6:
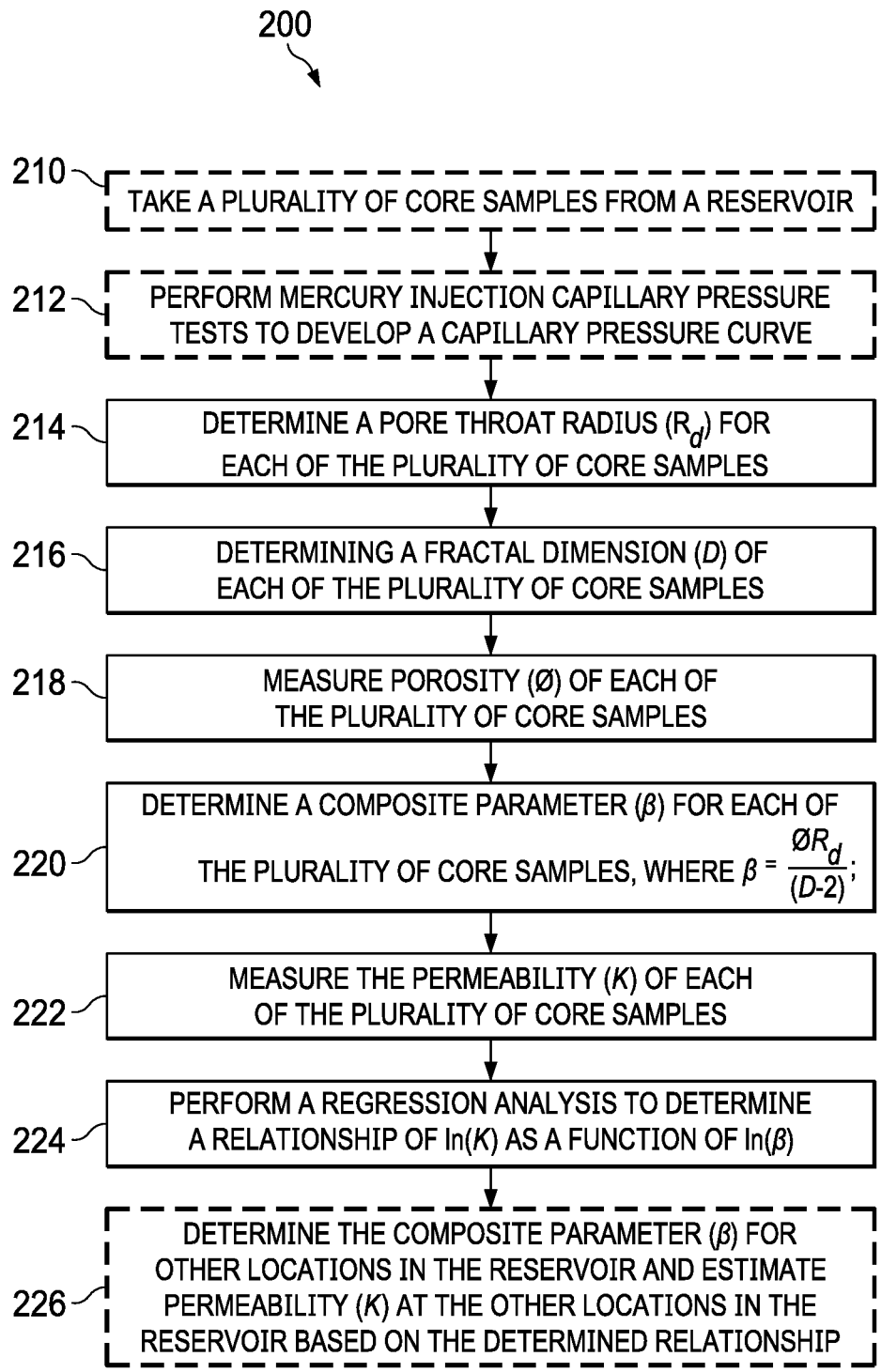
FIG. 6 is flow chart illustrating a method of estimating permeability of reservoir rocks using MICP data.

FIG. 6 is flow chart illustrating a method 200 of estimating permeability of reservoir rocks using MICP data. The method 200 includes receiving MICP test data and porosity data for a core sample. For many fields, MICP data is available on special core analysis datasets that are commonly used by oil companies. A fractal dimension (D) for the core sample, a pore throat radius ($R_d$), and a composite parameter (β) for the core sample where $$\beta = \frac{\phi R_d}{(D-2)}$$

are determined based on the received MICP test data for the core sample. Porosity is usually provided as a routine with conventional core analysis datasets. The composite parameter (β) for other locations in the reservoir can be determined after receiving historical MICP test data and determining a fractal dimension (D) of each of the other locations in the reservoir based on the received historical MICP test data for that location.

The permeability (K) of the core sample is then estimated based on a relationship of ln(K) as a function of ln(β) determined by performing a regression analysis data from other core samples from the reservoir.

In some implementations, the method 200 includes developing the relationship of ln(K) as a function of ln(β). In these implementations, the method 200 optionally includes taking a plurality of core samples from the reservoir (210). MICP tests are optionally performed to develop a capillary pressure curve for each of the plurality of core samples (212). In some implementations, the capillary pressure curve for each of the plurality of core samples is developed based on data from previously performed MICP tests. A pore throat radius ($R_d$) and a fractal dimension (D) are determined for each of the plurality of core samples (214). In some implementations, the pore throat radius ($R_d$) for each of the plurality of core samples is determined by determining an entry pressure of the largest pore subsystem from the MICP tests and calculating the associated the pore throat radius ($R_d$) using Washburn's equation. As previously discussed, the fractal dimension (D) of each of the plurality of core samples can be determined by determining a slope of a curve of ln $S_{Hg}$ as a function of ln $P_c$ where $S_{Hg}$ is mercury saturation and $P_c$ is capillary pressure (216).

The porosity (∅) of each of the plurality of core samples is measured or received (218). In some cases, the helium porosity (∅) of each of the plurality of core samples is measured. In some implementations, other approaches of measuring the porosity (∅) (e.g., optical methods under microscope, computed tomography method and using density-neutron log) are used.

The composite parameter (β) is determined for each of the plurality of core samples, where $$\beta = \frac{\phi R_d}{(D-2)}. \quad (220)$$

The permeability (K) of each of the plurality of core samples is measured (222). For example, liquid (e.g., water or oil) and gas (e.g., helium) permeability can be determined on core samples in the laboratory. A regression analysis is performed to determine a relationship of ln(K) as a function of ln(β) (224). This determined relationship can be used to estimate permeability (K) at the other locations in the reservoir after determining the composite parameter (β) for the other locations in the reservoir (226).

It is desirable that the plurality of core samples includes at least one core sample from multiple depositional textures present in the reservoir. In typical carbonate reservoirs, it is desirable that the plurality of core samples includes at least one grainstone core sample, at least one packstone core sample, at least one wackestone core sample, and at least one bindstone core sample.

Figure 7:
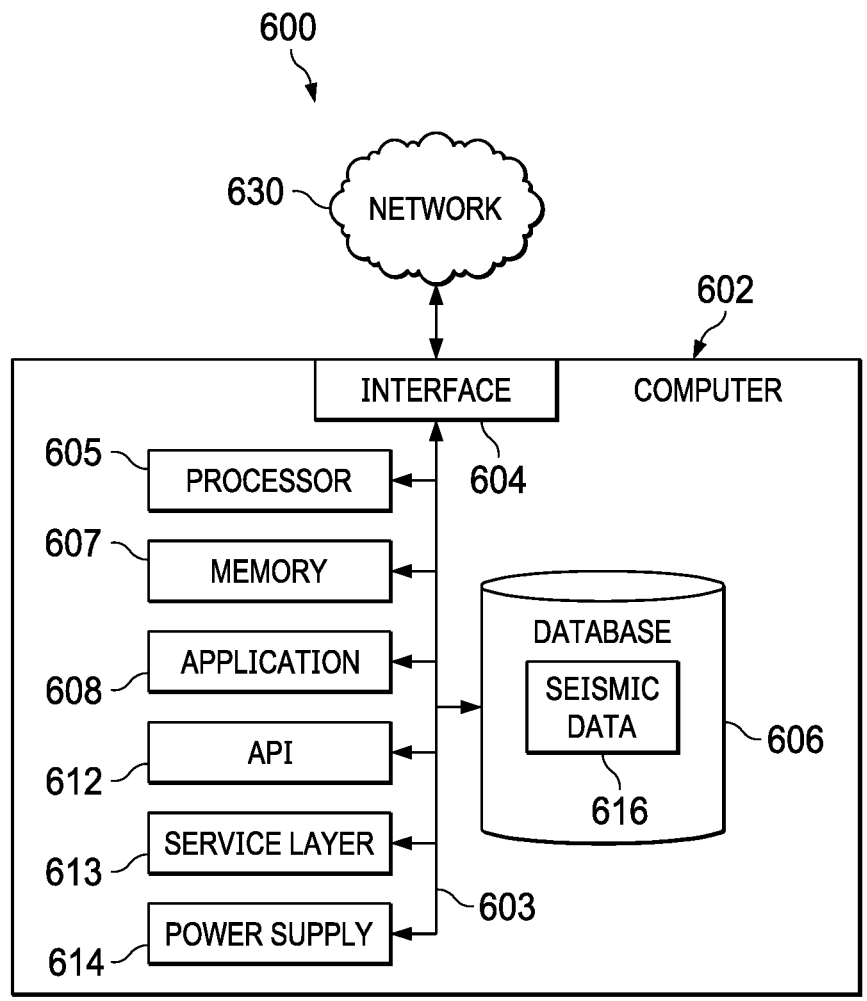
FIG. 7 is a block diagram illustrating an example computer system used to provide computational functionalities associated with described algorithms, methods, functions, processes, flows, and procedures according to some implementations of the present disclosure.

FIG. 7 is a block diagram of an example computer system 600 used to provide computational functionalities associated with described algorithms, methods, functions, processes, flows, and procedures described in the present disclosure, according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method of estimating permeability of reservoir rocks using mercury injection capillary pressure, the method comprising:
   taking a plurality of core samples from a reservoir;
   performing mercury injection capillary pressure tests to develop a capillary pressure curve for each of the plurality of core samples;
   determining a pore throat radius ($R_d$) for each of the plurality of core samples;
   determining a fractal dimension (D) of each of the plurality of core samples;
   measuring porosity (∅) of each of the plurality of core samples;
   determining a composite parameter (β) for each of the plurality of core samples, where $$\beta = \frac{\emptyset R_d}{(D-2)};$$

measuring the permeability (K) of each of the plurality of core samples;

performing a regression analysis to determine a relationship of ln(K) as a function of ln(β); and determining the composite parameter (β) for other locations in the reservoir and estimating permeability (K) at the other locations in the reservoir based on the determined relationship.

2. The method of claim 1, wherein determining a fractal dimension (D) of each of the plurality of core samples comprises determining a slope of a curve of ln $S_{Hg}$ as a function of ln $P_c$ where $S_{Hg}$ is mercury saturation and $P_c$ is capillary pressure.

3. The method of claim 1, wherein determining the composite parameter (β) for other locations in the reservoir comprises receiving historical mercury injection capillary pressure test data.

4. The method of claim 3, wherein determining the composite parameter (β) for other locations in the reservoir comprises determining a fractal dimension (D) of each of the other locations in the reservoir based on the received historical mercury injection capillary pressure test data for that location.

5. The method of claim 1, wherein the plurality of core samples includes at least one core sample from multiple depositional textures present in the reservoir.

6. The method of claim 5, wherein the plurality of core samples includes at least one grainstone core sample, at least one packstone core sample, at least one wackestone core sample, and at least one bindstone core sample.

7. The method of claim 1, wherein determining the pore throat radius ($R_d$) for each of the plurality of core samples comprises determining an entry pressure of the largest pore subsystem from the mercury injection capillary pressure tests and calculating the associated the pore throat radius ($R_d$) using Washburn's equation.

8. The method of claim 1, wherein measuring porosity (∅) of each of the plurality of core samples comprises measuring helium porosity (∅) of each of the plurality of core samples.

9. A method of estimating permeability of reservoir rocks using mercury injection capillary pressure, the method comprising:

receiving mercury injection capillary pressure test data and porosity data for a core sample;

determining a fractal dimension (D) for the core sample based on the received mercury injection capillary pressure test data for the core sample;

determining a pore throat radius ($R_d$) for the core sample;

determining a composite parameter (β) for the core sample where $$\beta = \frac{\emptyset R_d}{(D-2)};$$

and estimating permeability (K) of the core sample based on a relationship of ln(K) as a function of ln(β) determined by performing a regression analysis data from other core samples from the reservoir.

10. The method of claim 9, wherein the core sample is one of a plurality of core samples and receiving mercury injection capillary pressure test data and porosity data comprises receiving mercury injection capillary pressure test data and porosity data for each of the plurality of core samples.

11. The method of claim 10, wherein the plurality of core samples includes at least one core sample from multiple depositional textures present in the reservoir.

12. The method of claim 11, wherein the plurality of core samples includes at least one grainstone core sample, at least one packstone core sample, at least one wackestone core sample, and at least one bindstone core sample.

13. The method of claim 10, further comprising determining the pore throat radius ($R_d$) for each of the plurality of core samples.

14. The method of claim 13, wherein determining the pore throat radius ($R_d$) for each of the plurality of core samples comprises determining an entry pressure of the largest pore subsystem from the mercury injection capillary pressure tests and calculating the associated the pore throat radius ($R_d$) using Washburn's equation.

15. The method of claim 13, further comprising determining a fractal dimension (D) of each of the plurality of core samples.

16. The method of claim 15, wherein determining a fractal dimension (D) of each of the plurality of core samples comprises determining a slope of a curve of ln $S_{Hg}$ as a function of ln $P_c$ where $S_{Hg}$ is mercury saturation and $P_c$ is capillary pressure.

17. The method of claim 15, further comprising measuring porosity (∅) of each of the plurality of core samples.

18. The method of claim 17, further comprising determining a composite parameter (β) for each of the plurality of core samples, where $$\beta = \frac{\emptyset R_d}{(D-2)}.$$

19. The method of claim 18, further comprising measuring the permeability (K) of each of the plurality of core samples.

20. The method of claim 19, further comprising performing a regression analysis to determine a relationship of ln(K) as a function of ln(β).

* * * * *